United States Patent [19]

Han et al.

[11] Patent Number: 4,824,959

[45] Date of Patent: Apr. 25, 1989

[54] INTERMEDIATES FOR ANTIHYPERCHOLESTEROLEMIC TETRAZOLE COMPOUNDS

[75] Inventors: William T. Han, Cheshire; John J. Wright, Middletown, both of Conn.

[73] Assignee: Bristol-Myers Company, New York, N.Y.

[21] Appl. No.: 156,865

[22] Filed: Feb. 18, 1988

[51] Int. Cl.$^4$ ............................................. C07D 405/06
[52] U.S. Cl. ....................................... 548/253; 549/14
[58] Field of Search ........................................ 548/253

[56] References Cited

FOREIGN PATENT DOCUMENTS 332070 12/1986 European Pat. Off. .

*Primary Examiner*—David B. Springer
*Attorney, Agent, or Firm*—Aldo A. Algieri

[57] ABSTRACT

This invention provides novel intermediates of the formula

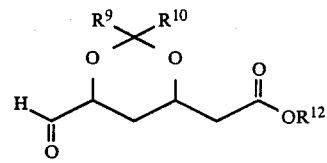

in substantially the cis or cis-(4R,6S) form wherein
$R^9$ and $R^{10}$ each are $C_{1-4}$alkyl or $R^9$ and $R^{10}$, taken together with the carbon atom to which they are attached, is cyclopentyl, cyclohexyl or cycloheptyl; and
$R^{12}$ is hydrogen, $C_{1-4}$alkyl or a metal cation
and processes thereof which are useful for the preparation of antihypercholesterolemic agents.

12 Claims, No Drawings

INTERMEDIATES FOR ANTIHYPERCHOLESTEROLEMIC TETRAZOLE COMPOUNDS

SUMMARY OF THE INVENTION

The present invention provides novel intermediates and processes for the preparation of compounds of the formulae

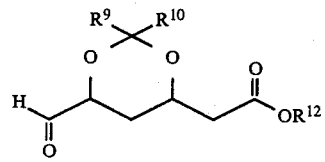

IIIa

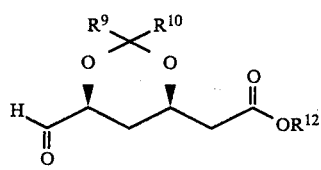

IIIb in substantially the cis form wherein $R^9$, $R^{10}$ and $R^{12}$ are as defined below which are useful for the preparation of inhibitors of the enzyme 3-hydroxy-3-methylglutaryl coenzyme A (HMG-CoA) reductase, and therefore, are useful in the treatment of hypercholesterolemia, hyperlipoproteinemia and atherosclerosis. The present invention also provides a simple and convenient chiral process for the preparation of inhibitors of HMG-CoA reductase and to certain chiral intermediates thereof.

DESCRIPTION OF THE INVENTION

The present invention provides intermediates which are useful for the preparation of antihypercholesterolemic agents, and which have the formulae

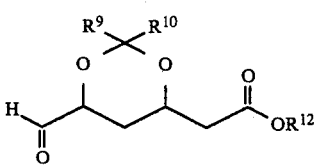

IIIa

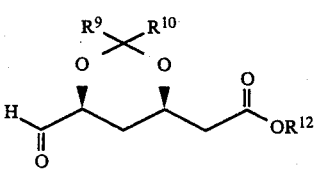

IIIb in substantially the cis form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation.

This invention also provides intermediates and processes for the preparation of the compounds of Formulae IIIa and IIIb and to intermediates and processes for the preparation of antihypercholesterolemic agents of the formulae

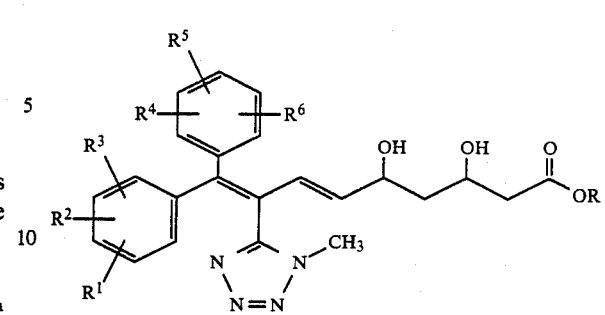

I

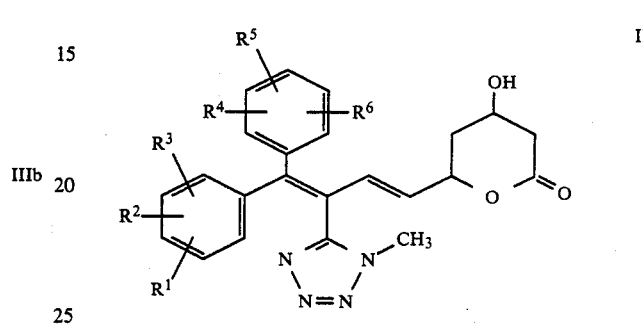

II wherein $R^1$ and $R^4$ each are independently hydrogen, halogen, $C_{1-4}$alkyl, $C_{1-4}$alkoxy or trifluoromethyl; $R^2$, $R^3$, $R^5$ and $R^6$ each are independently hydrogen, halogen, $C_{1-4}$alkyl or $C_{1-4}$alkoxy; and R is hydrogen, a hydrolyzable ester group or a cation to form a non-toxic pharmaceutically acceptable salt.

The terms "$C_{1-4}$alkyl", "$C_{1-6}$alkyl" and "$C_{1-4}$alkoxy" as used herein and in the claims (unless the context indicates otherwise) mean unbranched or branched chain alkyl or alkoxy groups such as methyl, ethyl, proply, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine while the term "halide" as used herein and in the claims is intended to include chloride, bromide and iodide anion. The term "a cation to form a non-toxic pharmaceutically acceptable salt" as used herein and in the claims is intended to include non-toxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as $C_{1-6}$alkyl, phenylmethyl and pivaloyloxymethyl.

In the compounds of formulae, I, II, XI and XII, it is intended that the double bonds are in the trans configuration, i.e., (E), as indicated in the structural formulae used herein and in the claims. Whereas in the compounds of Formulae IV, V, VI, VII, VIII and IX, it is intended that the configuration of the double bonds are trans, cis or mixtures thereof, i.e., (E), (Z) when n=o and (E)(E), (Z)(Z), (E)(Z) and (Z)(E) when n=1, as indicated herein and in the claims.

As the compounds of the present invention possess two asymmetric carbon atoms, the invention includes the enantiomeric and diastereomeric forms of the intermediates utilized in the processes for the prepraration of compounds of Formulae I and II as described herein and in the claims. The compounds of Formulae I and II which contain two centers of asymmetry may have four possible stereoisomers designated as the RR, RS, SR and SS enantiomers. Specifically, the compounds of Formula I having two asymmetric carbon atoms bearing the hydroxy groups in the 3 and 5 position may have four possible stereoisomers which are designated as the (3R,5S), (3S,5R), (3R,5R) and (3S,5S) stereoisomers. As used herein and in the claims, the term "erythro" is intended to include a mixture of (3R,5S) and (3S,5R) enantiomers, and the term "threo" is intended to include a mixture of (3R,5R) and (3S,5S) enantiomers. The use of single designation such as (3R,5S) is intended to include substantially one stereoisomer. The lactone compounds of Formual II also have two asymmetric carbon atoms at the 4 and 6 position, and the resulting four stereoisomers may be designated as the (4R,6S), (4S,6R), (4R,6R) and (4S,6S) stereoisomers. As used herein and in the claims, the term "trans" lactone is intended to include a mixture of (4R,6S) and (4S,6R) enantiomers while the term "cis" lactone is intended to include a mixture of (4R,6R) and (4S,6S) enantiomers. The use of a single designation such as (4R,6S) is intended to include substantially one enantiomeric lactone.

The substituted 1,3-dioxane compounds of Formula IIIa, IIIb and other similar compounds described herein and in the claims also contain two asymmetric carbon atoms at the 4 and 6 position as shown below,

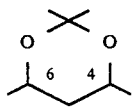

and the resulting four stereoisomers may be designated as the (4R,6S), (4S,6R), (4R,6R) and (4S,6S) stereoisomers. As used herein and in the claims, the term "trans"-1,3-dioxane is intended to include a mixture of (4R,6R) and (4S,6S) enantiomers while the term "cis"-1,3-dioxane is intended to include a mixture of (4R,6S) and (4S,6R) enantiomers. Since the most preferred enantiomer of the lactone compounds of Formula II has fortuitously the same (4R,6S) stereoisomeric designation as the most preferred enantiomer of the 1,3-dioxane intermediates of the present invention, the additional designation of "trans" or "cis" is included to avoid any possible confusion.

In the compounds of Formulae IIIa and IIIb, $R^9$ and $R^{10}$ each are $C_{1-4}$alkyl or $R^9$ and $R^{10}$, taken together with the carbon atom to which they are attached, is cyclopentyl, cyclohexyl or cycloheptyl. Preferably, $R^9$ and $R^{10}$ each are methyl or $R^9$ and $R^{10}$, taken together with the carbon atom to which they are attached, is cyclohexyl. It is preferred that $R^{12}$ is hydrogen, methyl or a metal cation especially lithium. The cis isomer of the compounds of Formula IIIa is preferred and the cis-(4R,6S) isomer of the compounds of Formula IIIb is most preferred.

The antihypercholesterolemic compounds of Formulae I and II may be prepared by various procedures and preferably by employing the intermediates of the formulae

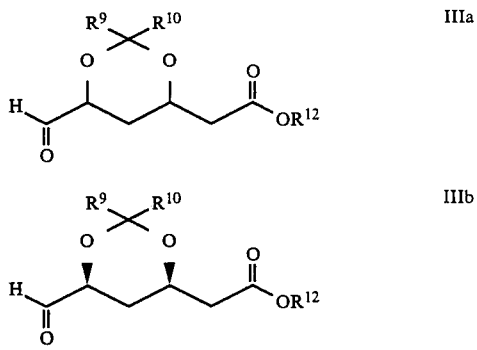

in substantially the cis form wherein $R^9$, $R^{10}$ and $R^{12}$ are as defined previously. Thus, the present invention provides a process for the preparation of the intermediates of Formulae IIIa and IIIb and also provides an improved processs for the preparation of compounds of the Formulae I and II.

The compounds of Formulae IIIa and IIIb may be prepared by the reaction of an aldehyde of Formula IV with an ester of acetoacetic acid and then reacting a ketone or ketal with a compound of Formula VI followed by hydrolysis of the resulting 1,3-dioxane of Formula VII and optionally resolving the acid of Formula VIII, as shown in Reaction Scheme 1.

Reaction Scheme 1

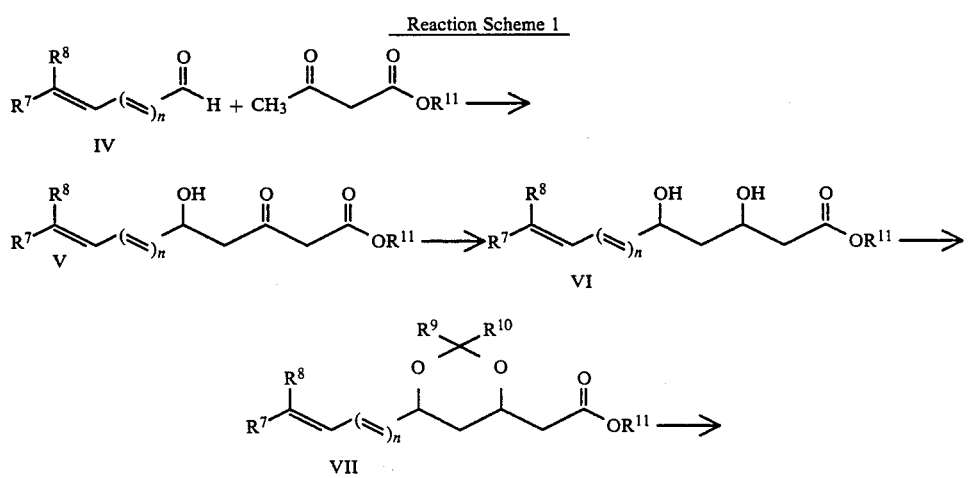

-continued
Reaction Scheme 1

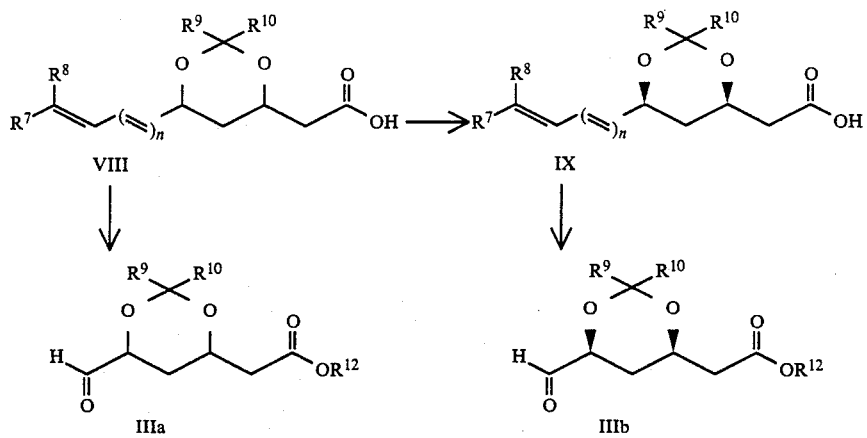

In Reaction Scheme 1, $R^7$ and $R^8$ each are independently hydrogen, $C_{1-6}$alkyl or phenyl which is optionally substituted by one or two $C_{1-4}$alkyl, halogen, $C_{1-4}$alkoxy or trifluoromethyl; $R^{11}$ is a hydrolyzable ester group, n is zero or 1 and $R^9$ and $R^{10}$ are as previously defined. The ketoester of Formula V may be prepared by the reaction of an ester of acetoacetic acid with an aldehyde of Formula IV by procedures well-known to those skilled in the art in an inert organic solvent such as tetrahydrofuran at temperatures of about 0° C. to about −78° C. in the presence of a base such as sodium hydride, lithium diisopropylamide and n-butyllithium.

The starting materials of Formula IV wherein n=0 and n=1 are known or may readily be prepared by known methods. The starting materials of Formula IV wherein n=1 may also be prepared by the reaction of compounds of Formula IV wherein n=0 with Wittig reagents such as triphenylphosphoranylidene acetaldehyde and other methods well-known in the art. It should be appreciated by those skilled in the art that the relative configuration of the double bond (n=0) or double bonds (n=1) in the starting materials of Formula IV may be trans, cis or mixtures thereof. The relative amounts of each geometric iosmer (E) or (Z) will be determined by commercial availability or the reaction conditions employed in the preparation. In a specific example described herein, a mixture containing mostly trans (E) isomer was employed. Even though a small percent of the other isomer may be present throughout the series of reactions shown in Reaction Scheme 1, it should be evident to those skilled in the art that the relative amount of isomers is not critical since the double bond is oxidized and thereby removed in the ozonolysis reaction.

The ketoester of Formula V may be reduced to the dihydroxyester of Formula VI by reduction of the ketone group with reducing agents well-known in the art. Preferably, the reduction is carried out in a stereospecific manner by a two-step stereospecific reduction in order to maximize the production of the preferred erythro isomer of the dihydroxyester of Formula VI. The stereospecific reduction is carried out with trisubstitutedalkylboranes, preferably triethylborane or tri-n-butylborane, or alkoxydialkylboranes, preferably methoxydiethylborane or ethoxydiethylborane [*Tetrahedron Letters*, 28, 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethylether and 1,2-dimethoxyethane, preferably tetrahydrofuran. The reduction is then completed by the addition of methanol with or without the addition of aqueous hydrogen peroxide and buffer. Some of the compounds of Formula VI are known and described in U.S. Pat. No. 4,248,889 (issued Feb. 3, 1981) and U.S. Pat. No. 4,650,890 (issued Mar. 17, 1987).

The compounds of Formula VII may be prepared from the compounds of Formula VI by reacting a ketone such as 2-propanone, 3-pentanone, cyclopentanone and cyclohexanone in a suitable inert organic solvent, e.g. toluene, benzene or xylene at temperatures of about 20° C. to the reflux temperature of the solvent employed in the presence of a small amount of organic, mineral or resin acid, e.g., p-toulenesulfonic acid and sulfuric acid and optionally removing the water which is formed with a drying agent, e.g., $Na_2SO_4$, $MgSO_4$ and molecular sieves or by azeotropical removal with a Dean-Stark trap or similar apparatus. The reaction of a compound of Formula VI with a ketone may also be carried out without solvent. Alternatively, the reaction described above of compounds of Formula VII may be carried out with a ketal such as 2,2-dimethoxypropane, 1,1-dimethoxycyclohexane and the like.

The compounds of Formula IIIa wherein $R^{12}$ is a hydrolyzable ester group, and preferably, $C_{1-4}$alkyl may be prepared from the corresponding compounds of Formula VII by oxidation of the olefinic group to an aldehyde group using conventional means. Alternatively, a compound of Formula VII is first hydrolyzed by basic hydrolysis to a compound of Formula VIII which is then oxidized to give a compound of Formula IIIa wherein $R^{12}$ is hydrogen. A particularly convenient oxidation method is the reaction of a compound of Formula VII or VIII in an inert organic solvent such as methanol, ethyl acetate and methylene chloride with ozone at temperatures of about −50° C. to about −78° C. When the reaction with ozone is complete as evidence by the color of the reaction mixture, the intermediate ozonide is decomposed by the addition of a mild reducing agent, e.g., dimethyl sulfide and triphenylphosphine to give the desired aldehyde of Formula IIIa.

The preferred cis-(4R,6S) aldehydes of Formula IIIb may be prepared from the corresponding racemic acid of Formula VIII by conventional resolution methods such as fractional crystallization after the introduction of a suitable salt-forming group. The resulting mixture of diastereoisomeric salts which is formed with an optically active salt-forming agent such as (1S,2R)-ephedrine and α-methylbenzylamine is separated and the separated resolved salt is converted to a compound of Formula IIIb. Preferably, the salt-forming agent is (1S,2R)-ephedrine and the method of separation is by fractional crystallization. The resolution may be carried out in an inert organic solvent, and preferably, in a mixture of hydrocarbon-alcohol solvents, e.g., hexane-methanol mixture, in which the resolved salt may crystallize from the solution. If it is desired, the acid of Formula IIIb may be converted to a salt wherein $R^{12}$ is a metal cation or to a hydrolyzable ester group wherein $R^{12}$ is $C_{1-4}$alkyl.

The preferred antihypercholesterolemic compounds of Formulae I and II may be prepared from a compound of Formula IIIa or IIIb by the general procedures described herein, in U.S. patent application Ser. No. 018,542, filed Feb. 25, 1987 and the corresponding continuation-in-part U.S. patent application Ser. No. 151513 (CT-1888A), filed 2/18/88 (concurrently) by John J. Wright and Sing-Yuen Sit, and in the U.S. patent application Ser. No. 018,558, filed Feb. 25, 1987 and the corresponding continuation-in-part U.S. patent application Ser. No. 15152 (CT-1890A), filed 2/18/88 concurrently by John J. Wright, Sing-Yuen Sit, Neelakantan Balasubramanian and Peter J. Brown. The use of the aldehydes of Formula IIIa is shown in Reaction Scheme 2 and the use of the chiral aldehydes of Formula IIIb is shown in Reaction Scheme 3.

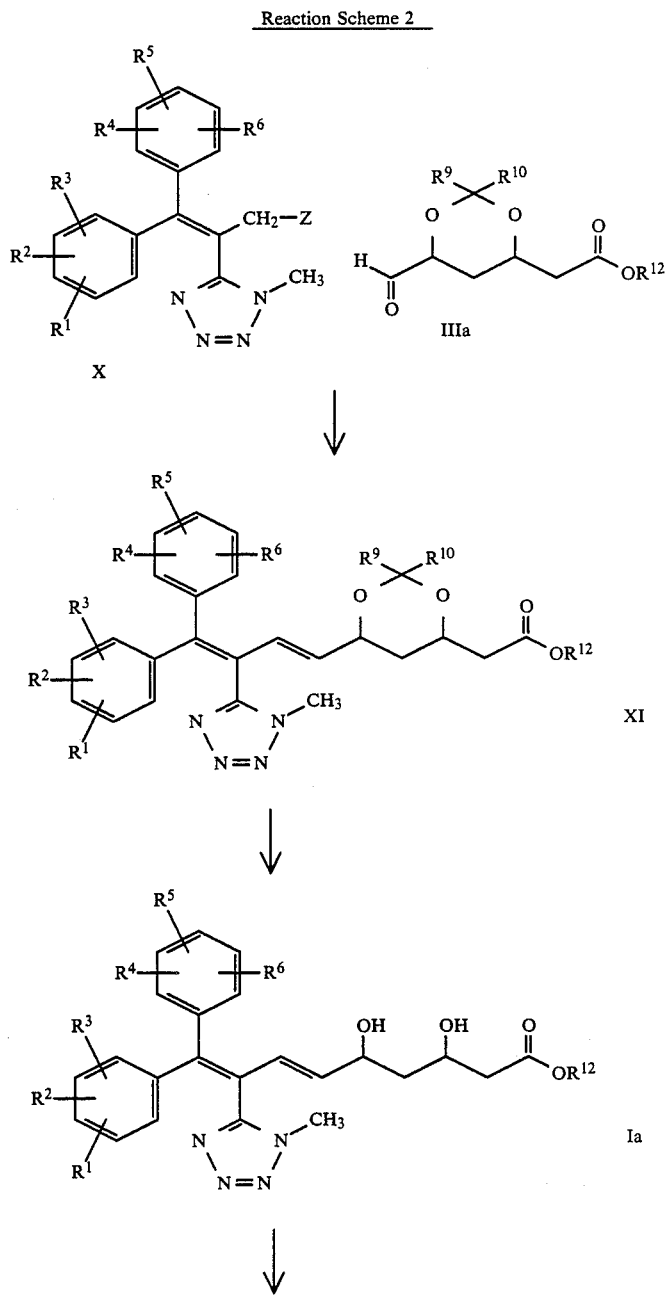

Reaction Scheme 2
Compound of Formula II

Reaction Scheme 3

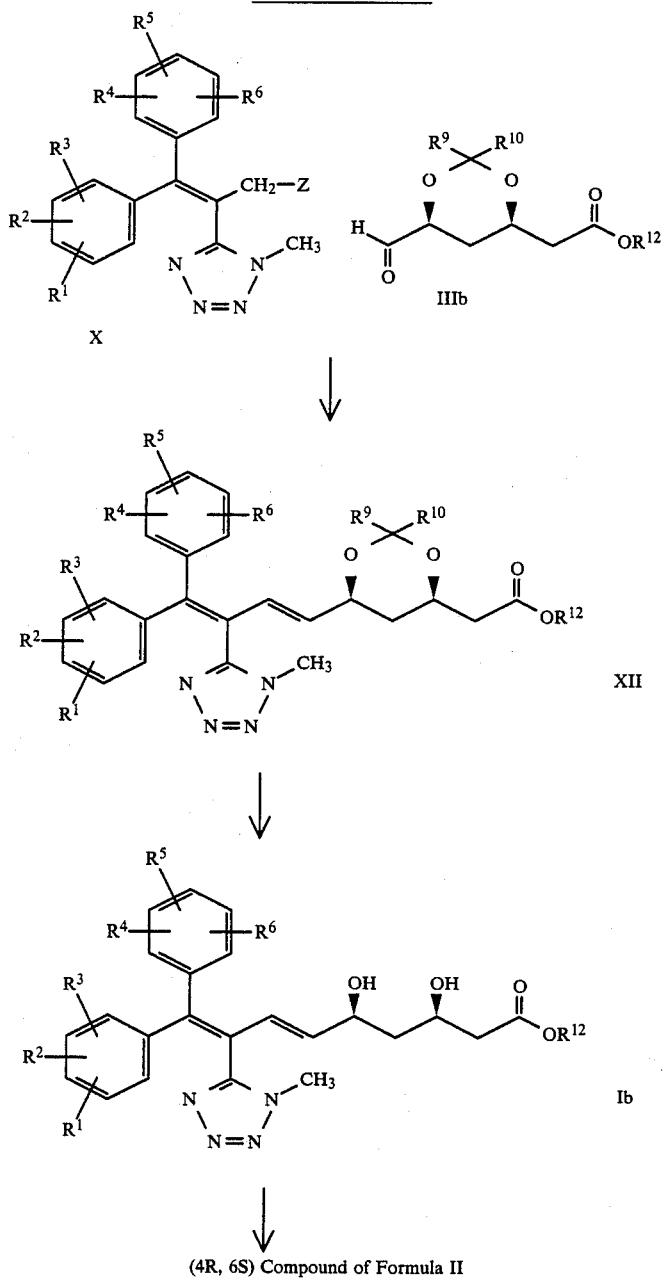

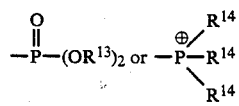
(4R, 6S) Compound of Formula II

In Reaction Schemes 2 and 3, $R^1$, $R^2$, $R^3$, $R^4$, $R^5$, $R^6$, $R^9$, $R^{10}$ and $R^{12}$ are as previously defined and Z is $$-\overset{O}{\underset{}{P}}-(OR^{13})_2 \text{ or } -\overset{\oplus}{P}\overset{R^{14}}{\underset{R^{14}}{-R^{14}}} \quad X^{\ominus}$$

in which $R^{13}$ is $C_{1-4}$alkyl, $R^{14}$ is phenyl which is unsubstituted or substituted by one or two $C_{1-4}$alkyl or chloro substituents and X is bromo, chloro or iodo. The phosphonium salt of Formula X and the phosphonate of Formula X is described herein, in U.S. patent application Ser. No. 018,558, filed Feb. 25, 1987 and in the continuation-in-part U.S. patent application Ser. No. 151512 (CT-1890A), filed 2/18/88 (concurrently) by one of us and colleagues Sing-Yuen Sit, Neelakantan Balasubramanian and Peter J. Brown. The reaction of a compound of Formula X with a compound of Formula IIIa or Formula IIIb to produce a compound of Formula XI or XII, respectively, wherein $R^{12}$ is $C_{1-4}$alkyl may be carried out in an inert organic solvent such as tetrahydrofuran and N,N-dimethylformamide in the presence of a strong base such as n-butyllithium at a temperature of about $-50°$ C. to about $-78°$ C. When the reaction of a compound of Formula X is carried out with a compound of Formula IIIa or IIIb wherein $R^{12}$ is hydrogen, it is preferred to use two equivalents of a strong base such as n-butyllithium. Alternatively, the salt of a compound of Formula IIIa or IIIb may be prepared which is then treated with a compound of Formula X and a strong base. The methods of addition, salt formation and ylide preparation are well-known to those skilled in the art. The tetrazole compounds of Formula XI or XII may be readily deprotected by well-known procedures such as mild acid, e.g., 0.2N HCl and 0.5N HCl in an inert organic solvent such as tetrahydrofuran to produce the erythro compounds of Formula Ia or the (3R,5S) compounds of Formula Ib which may then be converted to the trans compounds of Formula II or (4R,6S) compounds of Formula II in a conventional manner well-known to those skilled in the art.

In a preferred embodiment of the invention, the compounds of Formula IIIa have the structure

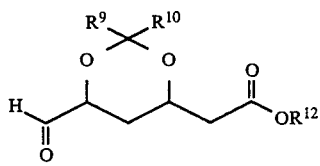

IIIa in substantially the cis form wherein $R^9$ and $R^{10}$ each are $C_{1-2}$alkyl or $R^9$ and $R^{10}$, taken together with the carbon atom to which they are attached, is cyclohexyl; and $R^{12}$ is hydrogen, $C_{1-2}$alkyl or a metal cation.

In a more preferred embodiment of the invention, the compounds of Formula IIIb have the structure

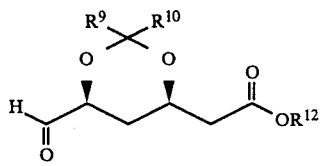

IIIb in substantially the cis-(4R,6S) form wherein $R^9$ and $R^{10}$ each are $C_{1-2}$alkyl or $R^9$ and $R^{10}$, taken together with the carbon atom to which they are attached, is cyclohexyl; and $R^{12}$ is hydrogen, $C_{1-2}$alkyl or a metal cation.

In another preferred embodiment of the invention, the compounds of Formula VIII have the structure

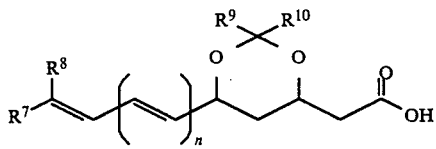

VIII in substantially the cis form wherein $R^7$ and $R^8$ each are independently hydrogen, $C_{1-6}$alkyl or phenyl; $R^9$ and $R^{10}$ each are $C_{1-2}$alkyl or $R^9$ and $R^{10}$, taken together with the carbon atom to which they are attached, is cyclohexyl; and n is zero or 1.

In another more preferred embodiment of the invention, the compounds of Formula IX have the structure

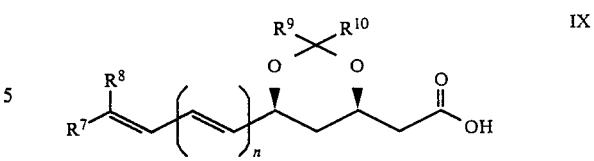

IX in substantially the cis-(4R,6S) form wherein $R^7$ and $R^8$ each are independently hydrogen, $C_{1-6}$alkyl or phenyl; $R^9$ and $R^{10}$ each are $C_{1-2}$alkyl or $R^9$ and $R^{10}$, taken together with the carbon atom to which they are attached, is cyclohexyl; and n is zero or 1.

In another aspect, this invention provides novel intermediates of the formula

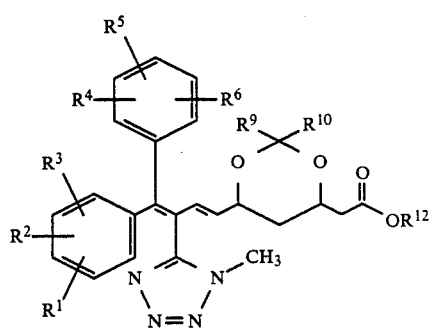

XI in substantially the cis form wherein $R^1$ and $R^4$ each are independently hydrogen, halogen, $C_{1-4}$alkyl, $C_{1-4}$alkoxy or trifluoromethyl; $R^2$, $R^3$, $R^5$ and $R^6$ each are independently hydrogen, halogen, $C_{1-4}$alkyl or $C_{1-4}$alkoxy; $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation.

In a preferred embodiment, this invention provides intermediates of Formula XI in substantially the cis form wherein $R^1$, $R^2$, $R^3$, $R^4$, $R^5$ and $R^6$ each are independently hydrogen, fluoro, chloro, methyl or methoxy; $R^9$ and $R^{10}$ each are $C_{1-2}$alkyl or $R^9$ and $R^{10}$, taken together with the carbon atom to which they are attached is cyclohexyl and $R^{12}$ is hydrogen, $C_{1-4}$alkyl or a metal cation.

In another preferred embodiment, this invention provides novel intermediates of the formula

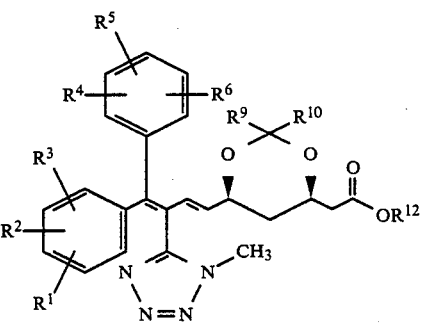

XII in substantially the cis-(4R,6S) form wherein $R^1$ and $R^4$ each are independently hydrogen, halogen, $C_{1-4}$alkyl, $C_{1-4}$alkoxy or trifluoromethyl; $R^2$, $R^3$, $R^5$ and $R^6$ each are independently hydrogen, halogen, $C_{1-4}$alkyl or $C_{1-}$ $_4$alkoxy; $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation.

In another more preferred embodiment, this invention provides intermediates of Formula XII in substantially the cis-(4R,6S) form wherein $R^1$, $R^2$, $R^3$, $R^4$, $R^5$ and $R^6$ each are independently hydrogen, fluoro, chloro, methyl or methoxy; $R^9$ and $R^{10}$ each are $C_{1-2}$alkyl or $R^9$ and $R^{10}$, taken together with the carbon atom to which they are attached, is cyclohexyl and $R^{12}$ is hydrogen, $C_{1-4}$alkyl or a metal cation.

In still another aspect, this invention provides a process for the preparation of an aldehyde of the formula

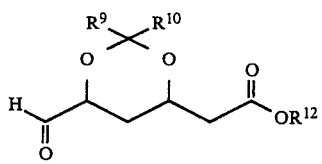   IIIa in substantially the cis form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation, comprising the steps of (a) reacting a dihydroxy compound of the formula

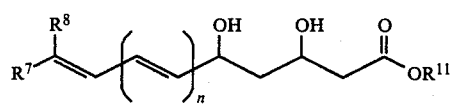   VI in substantially the erythro form wherein $R^7$ and $R^8$ each are independently hydrogen, $C_{1-6}$alkyl or phenyl which is optionally substituted by one or two $C_{1-4}$alkyl, halogen, $C_{1-4}$alkoxy or trifluoromethyl; $R^{11}$ is a hydrolyzable ester group; and n is zero or 1, in the presence of a small amount of acid with at least one equivalent of a compound of formula

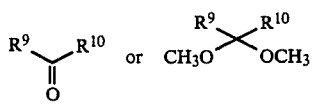

wherein $R^9$ and $R^{10}$ are as defined above, to produce a compound of the formula

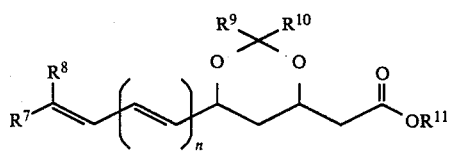   VII wherein $R^7$, $R^8$, $R^9$, $R^{10}$, $R^{11}$ and n are as defined above;

(b) optionally hydrolyzing an ester of Formula VII to produce a compound of Formula VIII

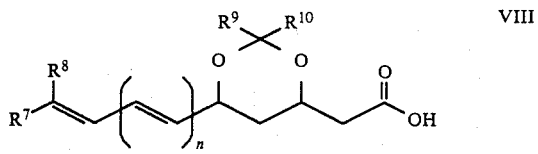   VIII wherein $R^7$, $R^8$, $R^9$ and $R^{10}$ are as defined above; and (c) oxidizing a compound of Formula VII or a compound of Formula VIII to produce a compound of the formula

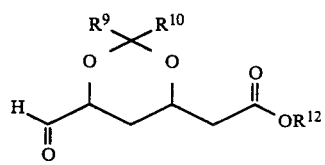   IIIa in substantially the cis form wherin $R^9$, $R^{10}$ and $R^{12}$ are as defined above.

In a preferred embodiment, this invention provides a process for the preparation of an aldehyde of the formula

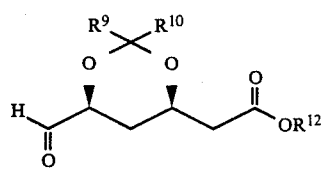   IIIb in substantially the cis-(4R,6S) form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation, comprising the steps of (a) reacting a dihydroxy compound of the formula

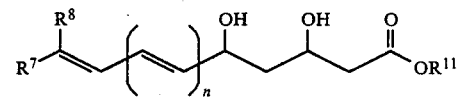   VI in substantially the erythro form wherein $R^7$ and $R^8$ each are independently hydrogen, $C_{1-6}$alkyl or phenyl which is optionally substituted by one or two $C_{1-4}$alkyl, halogen, $C_{1-4}$alkoxy or trifluoromethyl; $R^{11}$ is a hydrolyzable ester group; and n is zero or 1, in the presence of a small amount of acid with at least one equivalent of a compound of formula

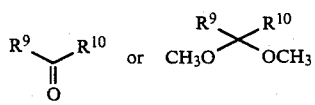

wherein $R^9$ and $R^{10}$ are as defined above, to produce a compound of the formula

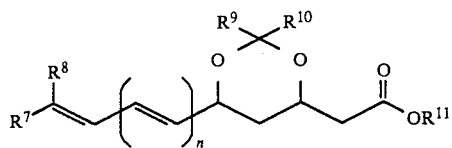

VII wherein $R^7$, $R^8$, $R^9$, $R^{10}$, $R^{11}$ and n are as defined above;

(b) hydrolyzing an ester of Formula VII to produce a compound of the formula

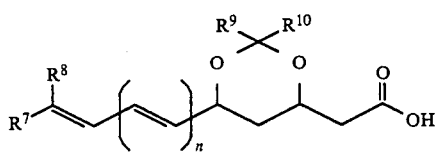

VIII wherein $R^7$, $R^8$, $R^9$, $R^{10}$ and n are as defined above;

(c) resolving the acid of Formula VIII to produce a compound of the formula

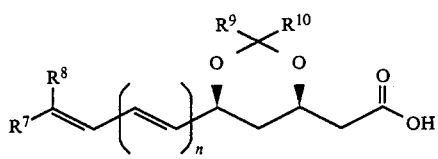

IX in substantially the cis-(4R,6S) form wherein $R^7$, $R^8$, $R^9$, $R^{10}$ and n are as defined above; and (d) oxidizing the acid of Formula IX and optionally preparing the ester thereof to produce a compound of the formula

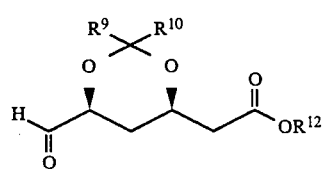

IIIb in substantially the cis-(4R,6S) form wherein $R^9$, $R^{10}$ and $R^{12}$ are as defined above.

In still a further aspect, this invention provides a process for the preparation of a compound of the formula

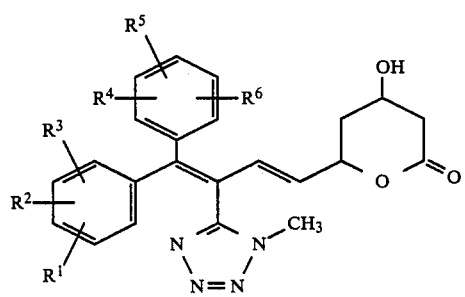

in substantially the trans form wherein $R^1$ and $R^4$ each are independently hydrogen, halogen, $C_{1-4}$alkyl, $C_{1-4}$alkoxy, or trifluoromethyl; and $R^2$, $R^3$, $R^5$ and $R^6$ each are independently hydrogen, halogen, $C_{1-4}$alkyl or $C_{1-4}$alkoxy, comprising the steps of (a) reacting a compound of the formula

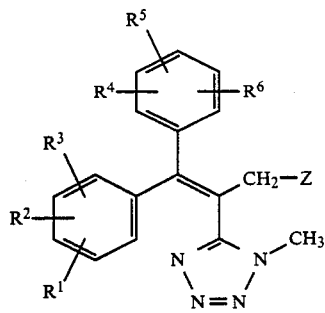

X wherein $R^1$, $R^2$, $R^3$, $R^4$, $R^5$ and $R^6$ are as defined above and Z is

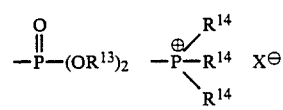

wherein $R^{13}$ is $C_{1-4}$alkyl; $R^{14}$ is phenyl which is unsubstituted or substituted by one of two $C_{1-4}$alkyl or chloro substituents; and X is bromo, chloro or iodo with a compound of the formula

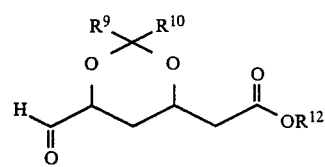

IIIa in substantially the cis form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation, to produce a compound of the formula

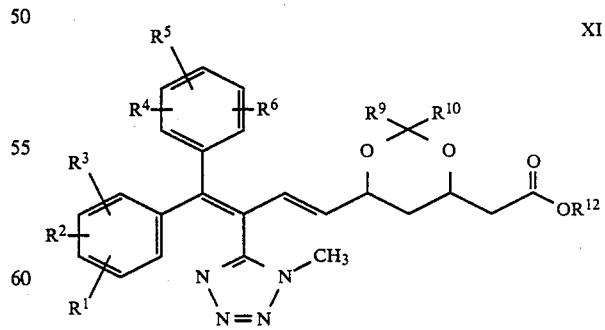

XI in substantially the cis form wherein $R^1$, $R^2$, $R^3$, $R^4$, $R^5$, $R^6$, $R^9$, $R^{10}$ and $R^{12}$ are as defined above;

(b) reacting a compound of Formula XI with acid to produce a compound of the formula

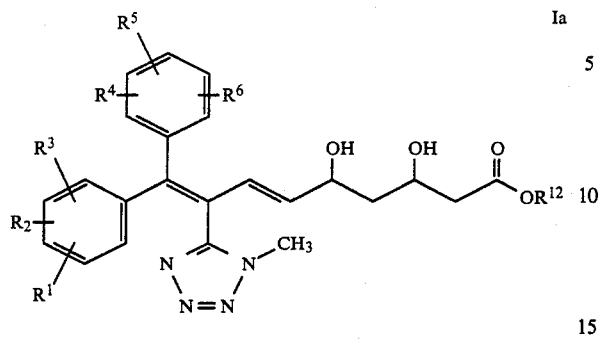

wherein $R^1$, $R^2$, $R^3$, $R^4$, $R^5$, $R^6$ and $R^{12}$ are as defined above; and (c) cyclizing a compound of Formula Ia wherein $R^{12}$ is hydrogen, to produce a compound of formula

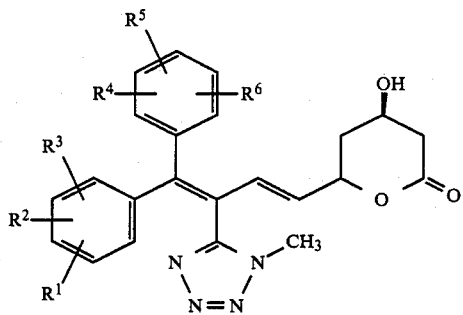

in substantially the trans form wherein $R^1$, $R^2$, $R^3$, $R^4$, $R^5$ and $R^6$ are as defined above.

In a preferred embodiment, this invention provides a process for the preparation of a compound of the formula

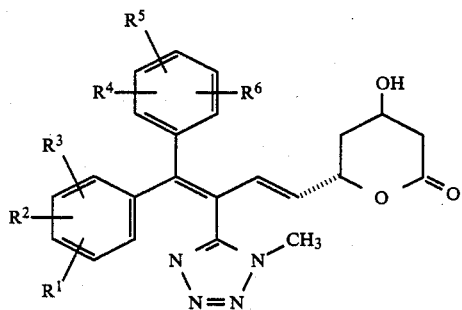

in substantially the trans-(4R,6S) form wherein $R^1$ and $R^4$ each are independently hydrogen, halogen, $C_{1-4}$alkyl, $C_{1-4}$alkoxy, or trifluoromethyl; and $R^2$, $R^3$, $R^5$ and $R^6$ each are independently hydrogen, halogen, $C_{1-4}$alkyl or $C_{1-4}$alkoxy, comprising the steps of (a) reacting a compound of the formula

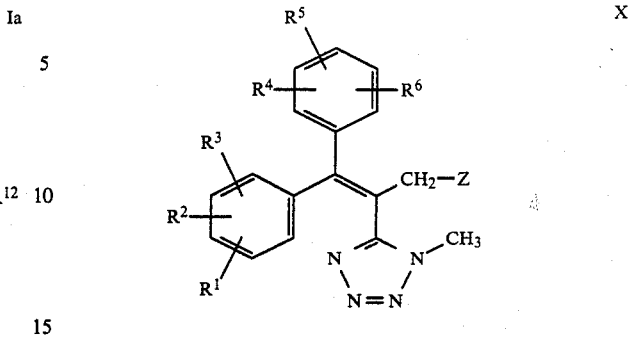

wherein $R^1$, $R^2$, $R^3$, $R^4$, $R^5$ and $R^6$ are as defined above and Z is

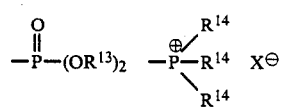

wherein $R^{13}$ is $C_{1-4}$alkyl; $R^{14}$ is phenyl which is unsubstituted or substituted by one or two $C_{1-4}$alkyl or chloro substituents; and X is bromo, chloro or iodo with a compound of the formula

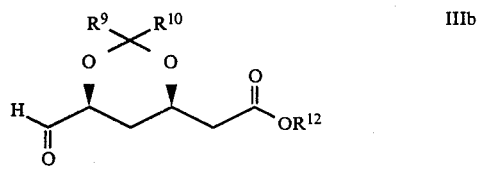

in substantially the cis-(4R,6S) form wherein $R^9$ and $R^{10}$ each are $C_{1-4}$alkyl or $R^9$ and $R^{10}$, taken together with the carbon atom to which they are attached, is cyclopentyl, cyclohexyl or cycloheptyl; and $R^{12}$ is hydrogen, $C_{1-4}$alkyl or a metal cation, to produce a compound of the formula

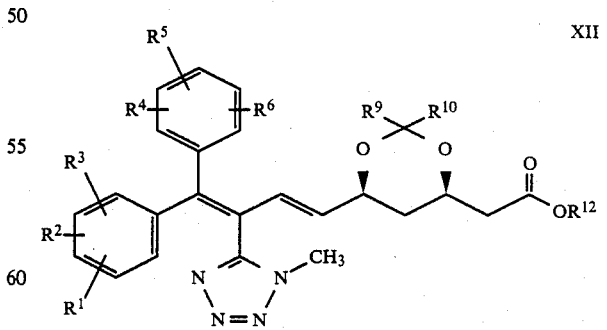

in substantially the cis-(4R,6S) form wherein $R^1$, $R^2$, $R^3$, $R^4$, $R^5$, $R^6$, $R^9$, $R^{10}$ and $R^{12}$ are as defined above;

(b) reacting the compund of Formula XII with acid to produce a compound of the formula

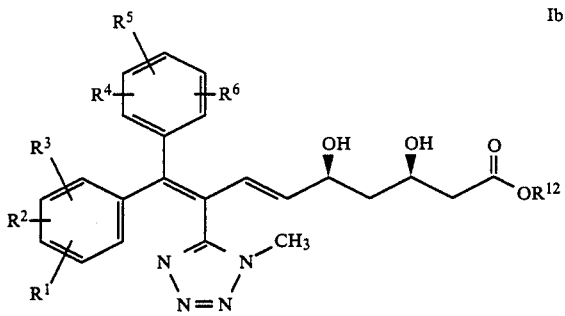

wherein $R^1$, $R^2$, $R^3$, $R^4$, $R^5$, $R^6$ and $R^{12}$ are as defined above; and (c) cyclizing the compound of Formula Ib wherein $R^{12}$ is hydrogen, to produce a compound of formula

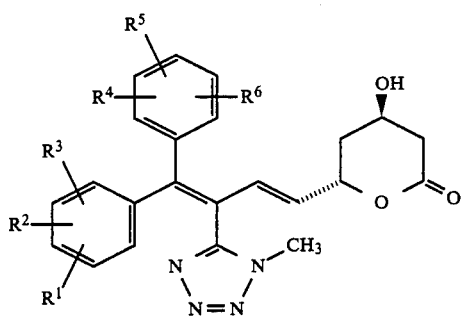

in substantially the trans-(4R,6S) form wherein $R^1$, $R^2$, $R^3$, $R^4$, $R^5$ and $R^6$ are as defined above.

In Vivo Acute Cholesterol Biosynthesis Inhibition in Rats

Male Wistar rats (160–200 g, housed 2 per cage) were maintained on normal diet (Purina Rat Chow and water, ad libitum) for at least 7 days on a reversed lighting schedule (7:00 a.m. to 5:00 p.m. dark). Food was removed 15 hours prior to dosing. Compounds were administered at 8:00 a.m. by intragastric intubation using 0.5–1.0 mL of water or propylene glycol solutions of sodium salts, lactones, or esters of the test compounds. Controls received equal volumes of the vehicle.

Thirty minutes after receiving the test substances, rats were injected intraperitoneally with 0.9 mL of 0.9% NaCl containing approximately 120 uCi per kg body weight of sodium[1-$^{14}$C]acetate (1–3 mCi/mol). After a 60 minute incorporation period, rats were sacrificed and liver and blood samples were obtained. Aliquots of plasma (1.0 mL) obtained by centrifugation of heparin- +EDTA-treated blood, and aliquots of liver homogenates (equivalent to 0.50 g liver wet weight) were taken for determination of radiolabeled 3-hydroxy sterols. Sterol isolation for the liver samples followed the method of Kates in Techniques in Lipidology, (M. Kates, ed.) pp. 349, 360–363, North Holland Publ. Co., Amsterdam, 1972 while the plasma samples were directly saponified followed by isolation of the digitonin-precipitable sterols. $^{14}$C-labelled sterols were quantified by liquid scintillation counting (efficiency corrected). Mean percent inhibition of $^{14}$C incorporated into liver and into plasma cholesterol was calculated for groups of treated animals and compared to mean values for controls conducted simultaneously.

Therefore, the above test provides information on the ability of test substances to suppress the de novo biosynthesis of cholesterol in vivo in rats with oral dosing. For example, using the above test, the compound of Example 13 yielded a 50% Inhibitory Dose (ED$_{50}$) for both plasma and liver cholesterol, comparable to values obtained for mevinolin (lovastatin) using a similar procedure [Alberts, et al., Proc. Natl. Acad. Sci., 77, 3957–3961 (1980)].

DESCRIPTION OF SPECIFIC EMBODIMENTS

In the following examples, all temperatures are given in degrees Centigrade. Melting points were recorded on a Thomas-Hoover capillary melting point apparatus and are uncorrected. Proton magnetic resonance ($^1$H NMR) spectra were recorded on a Bruker AM 300, Bruker WM 360 or Varian T-60 CW spectrometer. All spectra were determined in CDCl$_3$, DMSO-d$_6$ or D$_2$O unless otherwise indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; and dq, doublet of quartet. Carbon-13 nuclear magnetic resonance ($^{13}$C NMR) spectra were recorded on a Bruker AM 300 or Bruker WM 360 spectrometer and were broad band proton decoupled. All spectra were determined in CDCl$_3$, DMSO-d$_6$ or D$_2$O unless otherwise indicated with internal deuterium lock and chemical shifts are reported in δ units downfield from tetramethylsilane. Infrared (IR) spectra were determined on a Nicolet MX-1 FT spectrometer from 4000 cm$^{-1}$ to 400 cm$^{-1}$, calibrated to 1601 cm$^{-1}$ absorption of a polystyrene film and are reported in reciprocal centimeters (cm$^{-1}$). Relative intensities are indicated as follows: s (strong), m (medium) and w (weak). Optical rotations $[\alpha]_D^{25}$ were determined on a Perkin-Elmer 241 polarimeter in CHCl$_3$ at the concentrations indicated.

Analytical thin-layer chromatography (TLC) was carried out on precoated silica gel plates (60F=254) and visualized using UV light, iodine vapors and/or staining with one of the following reagents: (a) methanolic or ethanolic phosphomolybdic acid (2%) and heating; (b) reagent (a) followed by 2% cobalt sulphate in 5M H$_2$SO$_4$ and heating. Column chromatography, also referred to as flash column chromatography, was performed in a glass column using finely divided silica gel (32–63 μm on silica gel-H) and pressures somewhat above atmospheric pressure with the indicated solvents. Ozonolysis reactions were done using a Welsbach ozonator style T-23. All evaporations of solvents were performed under reduced pressure. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

Cis-2,2-dimethyl-6-(2-phenylethenyl)-1,3-dioxane-4-acetic acid methyl ester

Methyl 3,5-dihydroxy-7-phenyl-6-enoate (98% diastereomeric purity) (2.37 g, 9.48 mmol) was stirred with 2,2-dimethoxypropane (20 mL) and a catalytic amount of p-toluenesulfonic acid for 16 hours. The solution was partitioned between diethyl ether and dilute aqueous sodium bicarbonate solution. The organic layer was dried (Na₂SO₄) and concentrated under reduced pressure to afford a yellow solid. After recrystallization from isopropyl ether, 1.70 g (62%) of the title compound was obtained as a white solid; m.p.=84–86.5° C.

Alternatively, 0.2 g of a solid sodium carbonate can be added to the 2,2-dimethoxypropane solution and the solution stirred vigorously. The solid is filtered through a fluted filter paper. The excess 2,2-dimethoxypropane is removed under reduced pressure to afford a yellow solid which is recrystallized from isopropyl ether.

¹H NMR (CDCl₃)δ: 7.37–7.19 (5H, m), 6.59 (1H, d, J=15.9 Hz), 6.14 (1H, dd, J=15.9, 6.4 Hz), 4.57–4.35 (1H, m), 4.42–4.35 (1H, m), 3.68 (3H, s), 2.58 (1H, d, J=15.6, 6.9 Hz), 2.14 (1H, dd, J=15.6, 6.3 Hz), 1.74–1.61 (1H, m), 1.52 (3H, s), 1.43 (3H, s), 1.45–1.35 (1H, m).

Anal. Calcd. for C₁₇H₂₂O₄: C, 70.32; H, 7.63 Found: C, 70.24; H, 7.69.

EXAMPLE 2

Cis-2,2-dimethyl-6-(2-phenylethenyl)-1,3-dioxane-4-acetic acid

A solution of 2,2-dimethyl-6-(2-phenylethenyl)-1,3-dioxane-4-acetic acid methyl ester (8.5 g, 29.3 mmol) in 1N NaOH (32 mL) and methanol (64 mL) was heated to reflux for 45 minutes. After evaporation under reduced pressure, the aqueous solution was washed once with diethyl ether and acidified with 1N HCl (33 mL). The precipitate was collected and recrystallized from ethyl acetate/isopropyl ether to afford 7.2 g (90%) of the title compound as a colorless solid; m.p.=153–155° C.

¹H NMR (CDCl₃)δ: 7.37–7.20 (5H, m), 6.60 (1H, d, J=16.0 Hz), 6.14 (1H, dd, J=16.0, 6.4 Hz), 4.59–4.54 (1H, m), 4.43–4.35 (1H, m), 2.62 (1H, dd, J=16.0, 7.2 Hz), 2.51 (1H, dd, J=16.0, 5.3 Hz), 1.77–1.72 (1H, m), 1.54 (3H, s), 1.46 (3H, s), 1.50–1.36 (1H, m).

Anal. Calcd. for C₁₆H₂₀O₄: C, 69.54; H, 7.30 Found: C, 69.20; H, 7.33.

EXAMPLE 3

Resolution of cis-2,2-dimethyl-6-(2-phenylethenyl)-1,3-dioxane-4-acetic acid

The racemic cis-2,2-dimethyl-6-(2-phenylethenyl)-1,3-dioxane-4-acetic acid (0.31 g, 1.1 mmol) (prepared in Example 2) was dissolved in a boiling solution of hexane/ethanol containing (1S,2R)-ephedrine (0.2 g, 1.1 mmol). The resulting solution was very slowly brought to room temperature to give 0.21 g (41.4%) of colorless chiral salt (the usage of diastereomerically pure seed crystal is recommended during the resolution): m.p.=170°–171° C.

The chiral acid was freed through an acidic workup (as described in Example 4) and its enantiomeric purity was determined to be 100% by ¹H NMR using L-phenyltrifluoromethyl carbinol as a chiral solvent. [α]$_D^{25}$=+5.45° (c=1, CHCl₃).

EXAMPLE 4

Cis-(4R,6S)-2,2-dimethyl-6-formyl-1,3-dioxane-4-acetic acid

The resolved salt of cis-2,2-dimethyl-6-(2-phenylethenyl)-1,3-dioxane-4-acetic acid and (1S,2R)-ephedrine (6.6 g, 14.9 mmol) (prepared in Example 3) was partitioned between 0.5N HCl (30 mL) and diethyl ether. The ether layer was washed with brine, dried (MgSO₄/Na₂SO₄), and concentrated under reduced pressure to afford 4.1 g (99.6%) of the free acid. This acid was dissolved in dry methylene chloride (100 mL) and ozone was passed through this solution at −78° C. until there was deep blue coloration. Excess ozone was removed by purging with nitrogen and the ozonide formed was decomposed by adding CH₃SCH₃ (5 mL) and warming the solution to room temperature and allowed to stand for 16 hours. The solution was concentrated under reduced pressure and the residue was dissolved in isoamyl ether (ca 100 mL). The benzaldehyde which was formed during the ozonolysis was azeotroped together with isoamyl ether under reduced pressure to afford the title compound.

¹H NMR (CDCl₃)δ: 9.57 (1H, s), 4.40–4.30 (2H, m), 2.60 (1H, dd, J=16.0, 7.0 Hz), 2.49 (1H, dd, J=16.0, 6.0 Hz), 1.88–1.83 (1H, m) 1.49 (3H, s), 1.46 (3H, s), 1.42–1.31 (1H, m).

EXAMPLE 5

Dimethyl [3,3-bis(4-fluorophenyl)-2-(1-methyl-1H-tetrazol-5-yl)-2-propen-1-yl] phosphonate A slurry of 3,3-bis(4-fluorophenyl)-1-bromo-2-(1-methyl-1H-tetrazol-5-yl)-2-propane (1.17 g, 3.0 mmol) and trimethyl phosphite (0.41 g, 3.3 mmol) was heated at 100° C. for 5 minutes. After cooling to ambient temperature, excess trimethylphosphite was removed in vacuo to give a light yellow solid. This solid was recrystallized from ethylacetate/hexane mixture to give the title compound as a pure white solid; m.p. =140°–141° C.

IR (KBr) ν$_{max}$: 1604, 1511 cm⁻¹; ¹H NMR (CDCl₃) δ: 7.7–6.8 (8H, m), 3.6 (3H, s), 3.5 (3H, s), 3.42 (3H, s), 3.2 (2H, d);

Anal. Calcd. for C₁₉H₁₉F₂O₃N₄P: C, 54.29; H, 4.56; N, 13.33 Found: C, 53.83; H, 4.48; N, 13.50.

EXAMPLE 6

Cis-(4R,6S)-6-[4,4-bis(4-fluorophenyl)-3-(1-methyl-1H-tetrazol-5-yl)-1,3-butadienyl]-2,2-dimethyl-1,3-dioxane-4-acetic acid The crude chiral acid prepared in Example 4 was dissolved in dry THF (50 mL) and the resulting solution was transferred to a 250 mL three-neck flask purged with nitrogen and equipped with a mechanical stirrer. After the solution was stirred vigorously and cooled to −78° C., n-BuLi (2.5M in hexane, 5.96 mL) was added dropwise. Toward the end of addition, the solution turned into a suspension of white solid-like gel.

A separate flask containing dimethyl [3,3-bis(4-fluorophenyl)-2-(1-methyl-1H-tetrazol-5-yl)-2-propen-1-yl] phosphonate (6.2 g, 14.7 mmol) (prepared in Example 5) in THF (50 mL) under a nitrogen atmosphere was cooled to −78° C. and n-BuLi (2.5M in hexane, 5.96 mL) was added slowly. The resulting red-brown solution was stirred for 15 minutes at −78° C. This solution of phosphonate anion was transferred through a double ended needle to the above vigorously stirred suspension at −78° C. containing the lithium salt of the chiral acid. After the addition, the resulting brown solution was stirred for 30 minutes at −78° C. and 16 hours at ambient temperature. The THF solution was partitioned between 0.5N HCl and ethyl acetate. The organic phase was washed with brine (2x), dried (Na₂SO₄), and concentrated under reduced pressure. The residue was chromatographed on silica gel (66:33:1/diethyl ether:hexane:acetic acid) to afford 3.80 g (51.6% overall yield from the initial ephedrine salt; toluene was employed to azeotrope the residual acetic acid) of the title compound as a yellow foam. $[\alpha]_D^{25} = +106.1°$ (c=2.23, CHCl$_3$).

$^1$H NMR (CDCl$_3$) δ: 7.24–6.82 (8H, m), 6.62 (1H, d, J=15.0 Hz), 5.32 (1H, dd, J=15.0, 5.7 Hz), 4.42–4.37 (1H, m), 4.30–4.23 (1H, m), 3.51 (3H, s), 2.53 (1H, dd, J=15.9, 7.0 Hz), 2.42 (1H, dd, J=15.9, 5.6 Hz), 1.62–1.57 (1H, m), 1.46 (3H, s), 1.33 (3H, s), 1.30–1.20 (1H, m).

EXAMPLE 7

Trans-(4R,6S)-6-[4,4-bis(4-fluorophenyl)-3-(1-methyl-1H-tetrazol-5-yl)-1,3-butadienyl]-tetrahydro-4-hydroxy-2H-pyran-2-one Cis-(4R,6S)-6-[4,4-bis(4-fluorophenyl)-3-(1-methyl-1H-tetrazol-5yl)-1,3-butadienyl]-2,2-dimethyl-1,3-dioxane-4-acetic acid (3.7 g, 7.45 mmol) was dissolved in a solution of THF (90 mL) and 0.2N HCl (60 mL) and allowed to stand for 16 hours. The solution was partitioned between ethyl acetate and water. The organic layer was washed with brine (2x), dried (Na$_2$SO$_4$), and concentrated under reduced pressure. The residue was dissolved in dry methylene chloride (60 mL) and stirred for 4 hours in the presence of 1-cyclohexyl-3-(2-morpholinomethyl) carbodiimide metho-p-toluenesulfonate (6.6 g, 15.6 mmol). The solution was concentrated under reduced pressure and the residue was partioned between ethyl acetate and water. The organic layer was dried (Na$_2$SO$_4$) and concentrated under reduced pressure. The residue was purified by chromatography on silica gel (1:1/ethyl acetate:diethyl ether). After recrystallization from ethyl acetate-hexane, 1.33 g (40.1%) of the title compound was obtained as a white solid; m.p.=172°–173° C. $[\alpha]_D^{25} = +237.8°$ (c=2.17, CHCl$_3$).

EXAMPLE 8

Methyl 3-hydroxy-5-oxo-6,8-decadienoate

To a cold (−30° C.) solution of methyl acetoacetate (41.5 g, 357 mmol) in THF (500 mL) was added lithium diisopropylamide (476 mL, 1.5M solution in cyclohexane, 714 mmol). The resultant solution was stirred for 15 minutes at −30° C. After cooling to −78° C., 2,4-hexadienal (34.3 g, 357 mmol) was added and the solution stirred for 10 minutes at −78° C. and for 16 hours at ambient temperature. The solution was concentrated under reduced pressure and the residual syrup was partitioned between 1N HCl and ethyl acetate. The organic layer was washed with brine (2x), dried (Na$_2$SO$_4$), and concentrated. The residue was purified by chromatography on silica gel (diethyl ether:hexane/2:1) to afford 18.5 g (24.4%) of the title compound as an oil.

$^1$H NMR for (E) (E) isomer (200 MHz, CDCl$_3$) δ: 6.3 (1H, dd, J=14.7, 11.9 Hz), 6.02 (1H, dd, J=14.7, 11.9 Hz), 5.75 (1H, dq, J=14.7, 6.4 Hz), 5.5 (1H, dd, J=18.7, 6.4 Hz), 4.74–4.5 (1H, m), 3.73 (3H, s), 3.51 (2H, s), 2.6 (2H, d, J=5.8 Hz), 1.77 (3H, d, J=6.4 Hz).

EXAMPLE 9

Methyl 3,5-dihydroxy-6,8-decadienoate

To a cold (−15° C.) solution of methyl 3-hydroxy-5-oxo-6,8-decadienoate (18.5 g, 86.9 mmol) in THF (300 mL) was added triethylborane (1M in THF, 113 mL, 113 mmol) and the solution was stirred for 20 minutes. After the mixture was cooled to −78° C., NaBH$_4$ (6 g, 159 mmol) and methanol (37.5 mL) were added. The solution was vigorously stirred for 30 minutes at −78° C. and at ambient temperature for 3 hours. The solvent was removed under reduced pressure and the residue was partitioned between 1N HCl and ethyl acetate. The organic layer was dried (Na$_2$SO$_4$) and concentrated. The residue was purified by chromatography on silica gel (diethyl ether:hexane/3:1) to afford 7.95 g (42.7%) of the title compound as a yellow oil.

$^1$H NMR for (E) (E) isomer (360 MHz, CDCl$_3$) δ: 6.18 (1H, dd, J=15.1, 10.4 Hz), 6.00 (1H, dd, J=15.1, 10.4 Hz), 5.69 (1H, dq, J=15.1, 7.0 Hz), 5.52 (1H, dd, J=15.1, 6.7 Hz), 4.46–4.37 (1H, m), 4.29–4.22 (1H, m), 3.69 (3H, s), 2.60–2.42 (2H, m), 1.72 (3H, d, J=7.0 Hz), 1.74–1.57 (2H, m).

EXAMPLE 10

Methyl cis-4-(1,3-pentadienyl)-1,5-dioxaspiro[5.5]undecane-2-acetate

Methyl 3,5-dihydroxy-6,8-decadienoate (7.6 g, 35.5 mmol) and p-toluenesulfonic acid (0.1 g) was added to cyclohexanone (10 g, 100 mmol) and stirred for 16 hours at ambient temperature. The yellow solution was loaded directly onto a silica gel column and the product eluted with diethyl ether:hexane (1:4). The appropriate fractions were combined to give 3.52 g (33.6%) of the title compound as a colorless oil.

$^1$H NMR for (E) (E) isomer (360 MHz), CDCl$_3$) δ: 6.16 (1H, dd, J=15.1, 10.6 Hz), 6.00 (1H, dd, J=15.1, 10.6 Hz), 5.71–5.65 (1H, dd, J=15.1, 6.5 Hz), 5.47 (1H, dd, J=15.1, 6.4 Hz), 4.44–4.39 (1H, m), 4.35–4.30 (1H, m), 3.66 (3H, s), 2.52 (1H, dd, J=1.54, 7.9 Hz), 2.30 (1H, dd, J=15.4, 6.5 Hz), 2.1–1.18 (12H, m), 1.72 (3H, d, J=6.5 Hz).

Anal. Calcd. for C$_{17}$H$_{26}$O$_4$: C, 69.36; H, 8.90 Found: C, 69.59; H, 9.16.

EXAMPLE 11

Cis-4-(1,3-pentadienyl)-1,5-dioxaspiro[5.5]undecane-2-acetic acid

Methyl 4-(1,3-pentadienyl)-1,5-dioxaspiro[5.5]undecane-2-acetate (3.5 g, 12.4 mmol) was heated to reflux in a solution of 1N NaOH (13 mL) and methanol (26 mL). Methanol was removed under reduced pressure and the remaining aqueous solution was acidified with 1N HCl and extracted with diethyl ether. The organic layer was dried (Na$_2$SO$_4$) and concentrated. The residual solid was recrystallized from ethyl acetate/hexane to afford 2.0 g (55.9%) of the title compound as a colorless solid; m.p.=144°–146.5° C.

$^1$H NMR (360 MHz, CDCl$_3$) δ: 6.18 (1H, dd, J=18.0, 12.5 Hz), 5.72 (1H, dq, J=18.0, 7.7 Hz), 5.99 (1H, dd, J=18.0, 12.5 Hz), 5.48 (1H, dd, J=18.0, 7.6 Hz), 4.45–4.37 (1H, m), 4.37–4.25 (1H, m), 2.56 (1H, dd, J=18.9, 8.8 Hz), 2.48 (1H, dd, J=18.9, 6.1 Hz), 2.60–1.30 (12H, m), 1.73 (3H, d, J=7.7 Hz).

Anal. Calcd. for C$_{16}$H$_{24}$O$_4$: C, 68.54; H, 8.62 Found: C, 68.36; H, 8.55.

EXAMPLE 12

Cis-4-[4,4-bis(4-fluorophenyl)-3-(1-methyl-1H-tetrazol-5-yl)-1,3-butadienyl]-1,5-dioxaspiro[5.5]undecane-2-acetic acid A. 4-Formyl-1,5-dioxaspiro[5.5]undecane-2-acetic acid Ozone was passed through a solution of 4-(1,3-pentadienyl)-1,5-dioxaspiro[5.5]undecane-2-acetic acid (570 mg, 2.0 mmol) in methylene chloride (25 mL) at −78°

C. After the solution had attained a blue color, nitrogen was passed through the solution to remove the excess ozone. Dimethyl sulfide (0.5 mL) was added and the solution was concentrated under reduced pressure to afford the title compound as a viscous oil which was used without further purification in the subsequent step.

$^1$H NMR (60 MHz, CDCl$_3$) δ: 9.57 (1H, s), 4.52–4.14 (2H, m), 2.60–2.31 (2H, m), 2.10–1.10 (12H, m).

B.

Cis-4-[4,4-bis(4-fluorophenyl)-3-(1-methyl-1H-tetrazol-5-yl)-1,3-butadienyl]-1,5-dioxaspiro-[5.5]undecane-2-acid To a solution of dimethyl [3,3-bis(4-fluorophenyl)-2-(1-methyl-1H-tetrazol-5-yl)-2-propenyl] phoshonate (1.7 g, 4 mmol) in THF (20 mL) at −78° C. was added n-BuLi (1.6 mL, 4 mmol, 2.5M in hexane). The resultant brown-red solution was stirred for 30 minutes at −78° C. Using a double ended needle, this solution was transferred to a solution containing 4-formyl-1,5-dioxaspiro[5.5]undecane-2-acetic acid (prepared in Step A) in THF (10 mL) and maintained at −78° C. After the transfer had been completed, the combined reaction mixture was stirred at −78° C. for 1 hour and at ambient temperature for 4 hours. The solution was then partitioned between 0.5N HCl and ethyl acetate. The organic layer was washed with brine (2x), dried (Na$_2$SO$_4$), and concentrated under reduced pressure. The residue was purified by chromatography on silica gel (diethyl ether:hexane:acetic acid/50:20:1) to afford 342 mg (31.9% overall yield) of the title compound as a yellow foam.

$^1$H NMR (360 MHz, CDCl$_3$) δ: 7.25–6.84 (8H, m), 6.66 (1H, d, J=16.0 Hz), 5.32 (1H, dd, J=16.0, 5.10 Hz), 4.45–4.25 (2H, m), 3.52 (3H, s), 2.56 (1H, dd, J=16.0, 7.6 Hz), 2.44 (1H, dd, J=16.0, 5.1 Hz), 1.89–1.17 (12H, m).

EXAMPLE 13

Trans-6-[4,4-bis(4-fluorophenyl)-3-(1-methyl-1H-tetrazol-5-yl)-1,3-butadienyl]-tetrahydro-4-hydroxy-2H-pyran-2-one A mixture of 4-[4,4-bis(4-fluorophenyl)-3-(1-methyl-1H-tetrazol-5-yl)-1,3-butadienyl]-1,5-dioxaspiro[5.5]undecane-2-acetic acid (280 mg, 0.52 mmol) in 20 mL of THF/0.5N HCl (1:1) was allowed to stand at ambient temperature for 26 hours. The solution was partitioned between brine and ethyl acetate. The organic layer was washed with brine (2x), dried (Na$_2$SO$_4$) and concentrated. The resultant foam (126 mg) was dissolved in dry methylene chloride (10 mL) and treated with 1-cyclohexyl-3-(2-morpholinomethyl) carbodiimide metho-p-toluenesulfonate (0.24 g). After 16 hours at ambient temperature, the solution was evaporated under reduced pressure and the residue was purified by silica gel chromatography using ethyl acetate as eluent. The appropriate fractions afforded 38 mg (16.6%) of the title compound as a colorless oil which is a racemic mixture of the compound of Example 7.

EXAMPLE 14

Methyl 2,2-dimethyl-6-formyl-1,3-dioxane-4-acetate

Cis-2,2-dimethyl-6-(2-phenylethenyl)-1,3-dioxane-4-acetic acid methyl ester (prepared in Example 1) was dissolved in methanol (10 mL) and ozone was passed through the solution at −78° C. until the color of the solution turned blue. The reaction mixture was purged with nitrogen to remove excess ozone then dimethyl sulfide was added and the temperature was allowed to warm up to room temperature. The reaction was evaporated in vacuo and the residual oil was purified by chromatography on silica gel using diethyl ether-hexane (3:1) as the eluent to afford the title compound.

$^1$H NMR (360 MHz, CDCl$_3$) δ: 9.53 (1H, s), 4.40–4.23 (2H, m), 3.69 (3H, s), 2.53 (1H, dd, J=15.8, 7.02 Hz), 2.37 (1H, dd, J=15.8, 5.98 Hz), 1.85–1.76 (1H, m), 1.44 (3H, s), 1.40 (3H, s), 1.35–1.23 (1H, m).

EXAMPLE 15

3,3-Bis(4-fluorophenyl)-1-bromo-2-(1-methyl-1H-tetrazol-5-yl)-2-propene

A. 5-Ethyl-1-methyl-1H-tetrazole

To a slurry of 1,5-dimethyltetrazole (4.9 g, 0.05 mole) in dry tetrahydrofuran (50 mL) was added 2.5M n-butyllithium in hexanes (20 mL, 0.05 mole) over a period of 15 minutes at −78° C. under an inert atmosphere. This mixture was stirred for 30 minutes and a yellowish precipitate formed during this time. Methyl iodide (3.7 mL, 0.06 mole) was then added over a period of 15 minutes. After stirring for an additional 30 minutes, the clear reaction mixture was diluted with water and extracted with ethyl acetate (3×50 mL). The aqueous layer was washed with chloroform (2×25 mL), and the combined organic layer was dried over sodium sulfate and concentrated under reduced pressure to give an oil. The oil was purified by distillation to give 5.2 g (92%) of the title compound; b.p.=89°–90° C. at 0.05 mm Hg.

$^1$H NMR (CDCl$_3$) δ: 4.05 (s, 3H), 2.86 (q, 2H), 1.41 (t, 3H);

$^{13}$C NMR (CDCl$_3$) δ: 156.0, 33.24, 16.75, 11.20.

B.

1,1-Bis(4-fluorophenyl)-2-(1-methyl-1H-tetrazol-5-yl)propanol

To a solution of 5-ethyl-1-methyl-1H-tetrazole (5.6 g, 0.05 mole) [Prepared in Step A] in 60 mL of dry tetrahydrofuran was added 2.5M n-butyllithium (20 mL, 0.05 mole) in hexane over 5 minutes at −78° C. (bath temperature) under an inerat atmosphere. The mixture was stirred for 30 minutes and a solution of 4,4′-difluorobenzophenone (10.8 g, 0.5 mole) in 25 mL of dry tetrahydrofuran was added over 5 minutes. This mixture was stirred for an additional 2 hours while the bath temperature was slowly warmed to −20° C. the reaction was quenched with 1N HCl and extracted with ethyl acetate (3×50 mL) and chloroform (3×50 mL). The combined organic layer was dried over sodium sulfate and concentrated under reduced pressure to give a white solid. The solid was purified by crystallization from ethanol-hexane to give 10.8 g (65%) of the title compound; m.p.=160°–161° C.

IR (KBr) ν$_{max}$: 3400 cm$^{-1}$;

$^1$H NMR (CDCl$_3$) δ: 7.8–7.02 (m, 8H), 5.95 (s, 1H), 4.65 (q, 1H), 3.98 (s, 3H), 1.29 (d, 2H).

$^{13}$C NMR (CDCl$_3$) δ: 162.57, 162.37, 159.14, 156.71, 142.48, 140.54, 128.25, 128.13, 127.52, 127.42, 114.67, 114.41, 114.38, 78.56, 36.99, 33.43, 14.52.

Anal. Calc. for C$_{17}$H$_{16}$F$_2$N$_4$O: C, 61.81; H, 4.88; N, 16.96 Found: C, 61.79; H, 4.90; N, 17.09.

C.
1,1-Bis(4-fluorophenyl)-2-(1-methyl-1H-tetrazol-5-yl)-1-propene

A slurry of 1,1-bis(4-fluorophenyl)-2-(1-methyl-1H-tetrazol-5-yl)propanol (8.25 g, 0.025 mole) "prepared in Step B" and 100 mg of p-toluene sulfonic acid monohydrate in xylene (60 mL) was heated to reflux with a Dean & Stark water collecting apparatus for a period of 12 hours. The reaction mixture was washed with 1N NaOH (10 mL) while it was warm and with water (100 mL). Concentration of the organic layer gave off-white crystals of product. This was purified by recrystallization from ethanol-hexane to give 7.1 g (91%) of the title compound as white crystals; m.p.=146°–147° C.

IR (KBr) $\nu_{max}$: 1575; 1500 cm$^{-1}$. $^1$H NMR (CDCl$_3$) δ: 7.42–6.85 (m, 8H), 3.53 (s, 3H), 2.14 (s, 3H);

$^{13}$C NMR (CDCl$_3$) δ: 163.37, 163.08, 160.13, 155.61, 144.60, 145.34, 136.7, 136.42, 136.24, 136.19, 131.65, 131.54, 131.11, 131.01, 119.53, 115.51, 115.27, 115.22, 33.50, 21.20.

Anal. Calcd. for C$_{17}$H$_{14}$F$_2$N$_4$: C, 65,37; H, 4.51; N, 17.94 Found: C, 65.64; H, 4.61; N, 18.09.

D.
3,3-Bis(4-fluorophenyl)-1-bromo-2-(1-methyl-1H-tetrazol-5-yl)-2-propene A slurry of 1,1-bis(4-fluorophenyl)-2-(1-methyl-1H-tetrazol-5-yl)-1-propene (61.46 g, 0.197 mole) [prepared in Step C], N-bromosuccinimide (35.06 g, 0.197 mole) and catalytic amount of azobis isobutyronitrile or benzoyl peroxide in carbon tetrachloride (1.2 liters) was heated to reflux in an inert atmosphere for a period of 2 hours. The reaction mixture was cooled to ambient temperature and the solid from the reaction was filtered. The filtrate was concentrated under reduced pressure and the solid obtained was recrystallized from toluene-hexane to give 72 g (93%) of the title compound as white crystals; m.p.=159°–160° C.

IR (KBr) $\nu_{max}$: 1600 cm$^{-1}$.

$^1$H NMR (CDCl$_3$) δ: 7.5–7.1 (m, 8H), 4.44 (s, 2H), 3.53 (s, 3H).

$^{13}$C NMR (CDCl$_3$) δ: 163.94, 163.74, 160.60, 160.45, 143.42, 149.68, 135.20, 135.15, 134.69, 131.43, 131.31, 130.90, 130.80, 119.57, 115.94, 115.77, 115.65, 115.50.

Anal. Calcd. for C$_{17}$H$_{13}$F$_2$BrN$_4$: C, 52.19; H, 3.34; N, 14.32 Found: C, 52.58; H, 3.47; N, 14.49.

EXAMPLE 16
[1,1-Bis(4-fluorophenyl)-2-(1-methyl-1H-tetrazol-5-yl)-1-propen-3-yl]triphenylphosphonium bromide A slurry of 3,3-bis(4-fluorophenyl)-1-bromo-2-(1-methyl-1H-tetrazol-5-yl)-2-propene (1.95 g, 0.005 mole) [prepared in Example 15, Step D] and triphenylphosphine (1.3 g, 0.005 mole) in cyclohexane (25 mL) was heated to reflux. The reaction mixture became a clear solution after 30 minutes and a white precipitate appeared after 1 hour. the mixture was heated for an additional 8 hours, cooled to ambient temperature and the solid was collected by filtration and washed with diethyl ether. This white powder was dried in vacuum at 50° C. to give 3.0 g (92%) of the title compound; m.p.=254°–255° C.

IR (KBr) $\nu_{max}$: 3450, 1600, 1500, 1425 cm$^{-1}$. $^1$H NMR (DMSO-d$_6$) δ: 7.92–6.80 (m, 23H), 4.94 (6d, 2H), 3.83 (s, 3H);

$^{13}$C NMR (DMSO-d$_6$) δ: 163.53, 163.36, 160.28, 160.87, 154.04, 153.89, 152.76, 135.11, 134.79, 134.16, 133.68, 133.54, 130.53, 130.45, 130.35, 130.21, 130.07, 118.02, 116.89, 116.18, 115.89, 115.62, 115.32, 111.43, 111.39, 34.22, 28.88, 28.22.

Anal. Calcd. for C$_{35}$H$_{28}$BrF$_2$N$_4$P: C, 64.31; H, 4.32; N, 8.57 Found: C, 64.02; H, 4.37; N, 8.89.

What is claimed is:

1. A compound of the formula

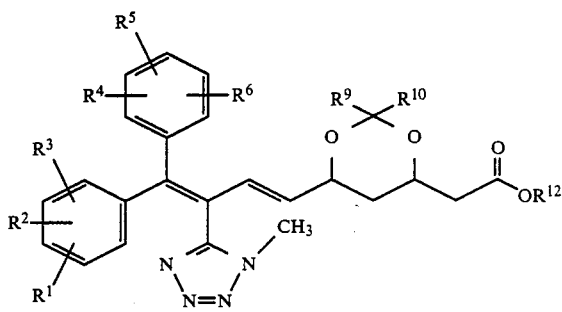

in substantially the cis form wherein

R$^1$ and R$^4$ each are independently hydrogen, halogen, C$_{1-4}$ alkyl, C$_{1-4}$ alkoxy or trifluoromethyl;

R$^2$, R$^3$, R$^5$ and R$^6$ each are independently hydrogen, halogen, C$_{1-4}$ alkyl or C$_{1-4}$ alkoxy;

R$^9$ and R$^{10}$ each are C$_{1-4}$ alkyl or R$^9$ and R$^{10}$, taken together with the carbon atom to which they are attached, is cyclopentyl, cyclohexyl or cycloheptyl; and R$^{12}$ is hydrogen, C$_{1-4}$ alkyl or a metal cation.

2. A compound of claim 1 having the formula

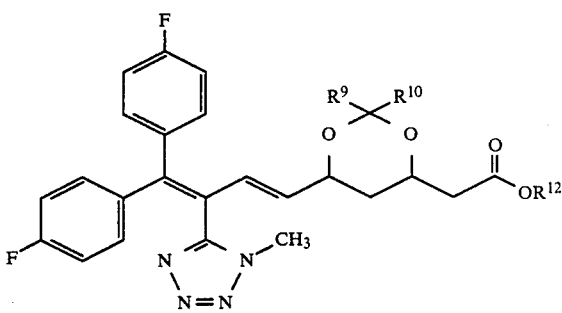

wherein

R$^9$ and R$^{10}$ each are C$_{1-4}$ alkyl or R$^9$ and R$^{10}$, taken together with the carbon atom to which they are attached, is cyclopentyl, cyclohexyl or cycloheptyl; and R$^{12}$ is hydrogen, C$_{1-4}$ alkyl or a metal cation.

3. A compound of claim 2 wherein R$^9$ and R$^{10}$ each are methyl; and R$^{12}$ is hydrogen, C$_{1-4}$alkyl or a metal cation.

4. The compound of claim 3 wherein R$^{12}$ is hydrogen.

5. A compound of claim 2 wherein R$^9$ and R$^{10}$, taken together with the carbon atom to which they are attached, is cyclohexyl; and R$^{12}$ is hydrogen, C$_{1-4}$ alkyl or a metal cation.

6. The compound of claim 5 wherein R$^{12}$ is hydrogen.

7. A compound of claim 1 having the formula

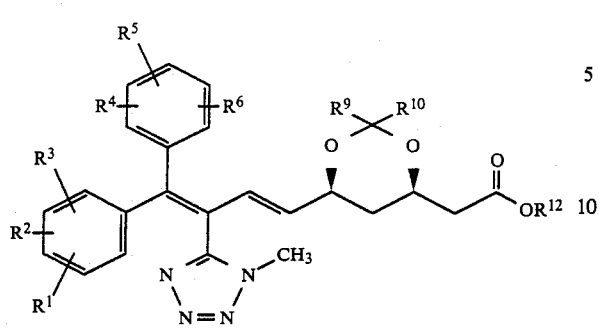

in substantially the cis-(4R,6S) form wherein $R^1$ and $R^4$ each are independently hydrogen, halogen, $C_{1-4}$ alkyl, $C_{1-4}$ alkoxy or trifluoromethyl;

$R^2$, $R^3$, $R^5$ and $R^6$ each are independently hdyrogen, halogen, $C_{1-4}$ alkyl, or $C_{1-4}$ alkoxy;

$R^9$ and $R^{10}$ each are $C_{1-4}$ alkyl or $R^9$ $R^{10}$, taken together with the carbon atom to which they are attached, is cyclopentyl, cyclohexyl or cycloheptyl; and $R^{12}$ is hydrogen, $C_{1-4}$ alkyl or a metal cation.

8. A compound of claim 7 having the formula

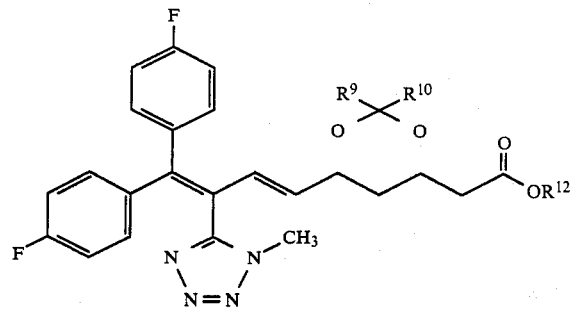

wherein $R^9$ and $R^{10}$ each are $C_{1-4}$ alkyl or $R^9$ and $R^{10}$, taken together with the carbon atom to which they are attached, is cyclopentyl, cyclohexyl or cycloheptyl; and $R^{12}$ is hydrogen, $C_{1-4}$ alkyl or a metal cation.

9. A compound of claim 8 wherein $R^9$ and $R^{10}$ each are methyl; and $R^{12}$ is hydrogen, $C_{1-4}$ alkyl or a metal cation.

10. The compound of claim 9 wherein $R^{12}$ is hydrogen.

11. A compound of claim 8 wherein $R^9$ and $R^{10}$, taken together with the carbon atom to which they are attached, is cyclohexyl; and $R^{12}$ is hydrogen, $C_{1-4}$ alkyl or a metal cation.

12. The compound of claim 11 wherein $R^{12}$ is hydrogen.

* * * * *